United States Patent [19]

Fleisch et al.

[11] Patent Number: 5,998,454
[45] Date of Patent: Dec. 7, 1999

[54] LEUKOTRIENE ANTAGONISTS USEFUL FOR TREATING IRITIS

[75] Inventors: Jerome H. Fleisch, Carmel; William T. Jackson; Jason S. Sawyer, both of Indianapolis, all of Ind.

[73] Assignee: Eli Lilly and Company, Indianapolis, Ind.

[21] Appl. No.: 09/042,350

[22] Filed: Mar. 13, 1998

Related U.S. Application Data

[60] Provisional application No. 60/040,873, Mar. 21, 1997.
[51] Int. Cl.$^6$ ............................ A61K 31/19; A61K 31/41
[52] U.S. Cl. .......................... 514/381; 514/318; 514/340; 514/343
[58] Field of Search ..................................... 514/381, 318, 514/340, 343

[56] References Cited

U.S. PATENT DOCUMENTS 5,462,954  10/1995  Baker et al. ............................ 514/381

OTHER PUBLICATIONS

Shindo, et al., *Current Therapeutic Research*, 53: 635–637 (1993).

*Primary Examiner*—Zohreh Fay
*Attorney, Agent, or Firm*—Nelsen L. Lentz

[57] ABSTRACT

This invention provides methods for the treatment or inhibiting of iritis which comprises administering to a mammal in need thereof an effective amount of a compound having activity as a leukotriene $B_4$ antagonist.

8 Claims, No Drawings

LEUKOTRIENE ANTAGONISTS USEFUL FOR TREATING IRITIS

This application claims the benefit of U.S. Provisional Patent Application Serial No. 60/040,873 filed Mar. 21, 1997.

BACKGROUND OF THE INVENTION

A red eye is a common complaint, often related to benign conditions. However, a red eye in conjunction with symptoms such as photophobia, pain and decreased visual acuity may be a much more serious disorder.

Intraocular inflammation may result in deleterious structural alterations such as cataracts, synchiae and glaucoma. It may also lead to microvascular leakage in the retina circulation.

Iritis or inflammation of the iris and conjunctivitis can be precipitated by a variety of causes. For example, in addition to infectious causes, allergies and hypersensivity may cause iritis and it occurs as a secondary complication in five to ten percent of patients with ulcerative colitis, and up to 30% of patients with ankylosing spondytitis.

Once the diagnosis is made, treatment with mydriatic and cycloplegic agents with topical corticosteriods is imperative. However, close monitoring is required because overuse of corticosteriods has ominous side effects.

Research in the area of allergic reactions of the lung has provided evidence that arachidonic acid derivatives formed by the action of lipoxygenases are related to various disease states. Some of these arachidonic acid metabolites have been classified as members of a family of eicosatetraenoic acids termed leukotrienes. Three of these substances are currently thought to be major components of what has been previously called slow reacting substance of anaphylaxis (SRS-A) and have been designated leukotrienes $C_4$, $D_4$, and $E_4$ ($LTC_4$, $LTD_4$, and $LTE_4$, respectively).

Another arachidonic acid metabolite, leukotriene $B_4$ ($LTB_4$), is a proinflammatory lipid which has been implicated in the pathogenesis of psoriasis, arthritis, chronic lung diseases, acute respiratory distress syndrome, shock, asthma, inflammatory bowel diseases, and other inflammatory states characterized by the infiltration and activation of polymorphonuclear leukocytes and other proinflammatory cells. Thus, when activated, the polymorphonuclear leukocytes liberate tissue-degrading enzymes and reactive chemicals causing the inflammation. Antagonism of $LTB_4$ should therefore provide a novel therapeutic approach to treatment of these and other $LTB_4$ mediated conditions.

Because of the debilitating effects of ophthalmic disorders such as iritis there continues to exist a need for effective treatments.

SUMMARY OF THE INVENTION

This invention provides a method for the treatment or inhibiting of iritis in mammals comprising administering to a mammal in need thereof an effective amount of a compound of Formula I

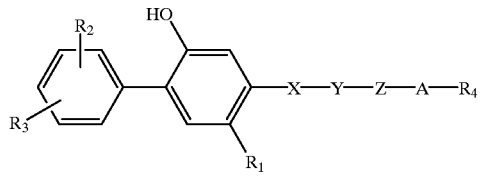

wherein:

$R_1$ is $C_1$–$C_5$ alkyl, $C_2$–$C_5$ alkenyl, $C_2$–$C_5$ alkynyl, $C_1$–$C_4$ alkoxy, ($C_1$–$C_4$ alkyl)thio, halo, or $R_2$-substituted phenyl;

each $R_2$ and $R_3$ are each independently hydrogen, halo, hydroxy, $C_1$–$C_4$ alkyl, $C_1$–$C_4$ alkoxy, ($C_1$–$C_4$ alkyl)-S(O)$_q$—, trifluoromethyl, or di-($C_1$–$C_3$ alkyl)amino;

X is —O—, —S—, —C(=O), or —CH$_2$—;

Y is —O— or —CH$_2$—;

or when taken together, -X-Y- is —CH=CH— or —C≡C—;

Z is a straight or branched chain $C_1$–$C_{10}$ alkylidenyl;

A is a bond, —O—, —S—, —CH=CH—, or —CR$_a$R$_b$-, where R$_a$ and R$_b$ are each independently hydrogen, $C_1$–$C_5$ alkyl, or R$_7$-substituted phenyl, or when taken together with the carbon atom to which they are attached form a $C_4$–$C_8$ cycloalkyl ring;

$R_4$ is $R_6$

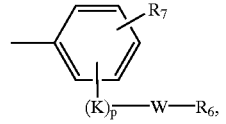

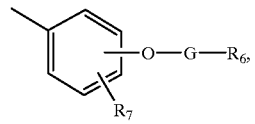

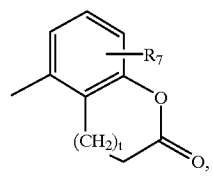

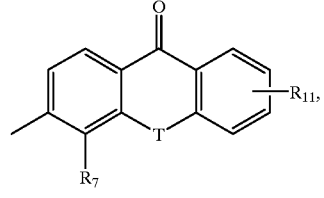

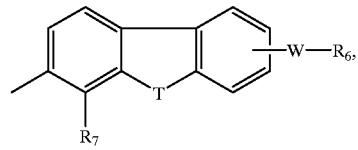

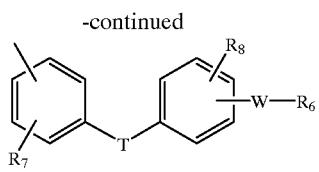

-continued where, each $R_6$ is independently —COOH, 5-tetrazolyl, —CON($R_9$)$_2$, or —CONHSO$_2R_{10}$;

each $R_7$ is hydrogen, $C_1$–$C_4$ alkyl, $C_2$–$C_5$ alkenyl, $C_2$–$C_5$ alkynyl, benzyl, methoxy, -W-$R_6$, -T-G-$R_6$, ($C_1$–$C_4$ alkyl)-T-($C_1$–$C_4$ alkylidenyl)-O—, or hydroxy;

$R_8$ is hydrogen or halo;

each $R_9$ is independently hydrogen, phenyl, or $C_1$–$C_4$ alkyl, or when taken together with the nitrogen atom form a morpholino, piperidino, piperazino, or pyrrolidino group;

$R_{10}$ is $C_1$–$C_4$ alkyl or phenyl;

$R_{11}$ is $R_2$, -W-$R_6$, or -T-G-$R_6$;

each W is a bond or straight or branched chain divalent hydrocarbyl radical of one to eight carbon atoms;

each G is a straight or branched chain divalent hydrocarbyl radical of one to eight carbon atoms;

each T is a bond, —CH$_2$—, —O—, —NH—, —NHCO—, —C(=O)—, or —S(O)$_q$—;

K is —C(=O)— or —CH(OH)—;

each q is independently 0, 1, or 2;

p is 0 or 1; and t is 0 or 1;

provided when X is —O— or —S—, Y is not —O—;

provided when A is —O— or —S—, $R_4$ is not $R_6$;

provided when A is —O— or —S— and Z is a bond, Y is not —O—; and provided W is not a bond when p is 0;

or a pharmaceutically acceptable salt or solvate thereof.

DETAILED DESCRIPTION

The following definitions refer to the various terms used throughout this disclosure.

The term "$C_1$–$C_5$ alkyl" refers to the straight and branched aliphatic radicals of 1 to 5 carbon atoms such as methyl, ethyl, propyl, isopropyl, n-butyl, sec-butyl, tert-butyl, n-pentyl, 2,2-dimethylpropyl, and the like. Included within this definition are the terms "$C_1$–$C_3$ alkyl" and "$C_1$–$C_4$ alkyl".

The term "$C_2$–$C_5$ alkenyl" refers to straight and branched aliphatic radicals of 2 to 5 carbon atoms containing one double bond, such as —CH=CH$_2$, —CH$_2$CH=CH$_2$, —CH$_2$CH$_2$CH=CH$_2$, —CH$_2$C(CH$_3$)=CH$_2$, —CH$_2$CH=C(CH$_3$)$_2$, and the like.

The term "$C_2$–$C_5$ alkynyl" refers to straight and branched aliphatic residues of 2 to 5 carbon atoms containing one triple bond, such as —C≡CH, —CH$_2$—C≡CH, —CH$_2$CH$_2$C≡CH, —CH$_2$CH(CH$_3$)C≡CH, —CH$_2$C≡CCH$_3$, and the like.

The term "$C_1$–$C_4$ alkoxy" refers to methoxy, ethoxy, propoxy, isopropoxy, butoxy, sec-butoxy, and tert-butoxy.

The term "halo" refers to fluoro, chloro, bromo, and iodo.

The term "$C_1$–$C_{10}$ alkylidenyl" refers to a divalent radical derived from a $C_1$–$C_{10}$ alkane such as —CH$_2$—, —CH(CH$_3$)—, —C(CH$_3$)$_2$—, —CH(C$_2$H$_5$)—, —CH$_2$CH$_2$—, —CH$_2$CH(CH$_3$)—, —CH(CH$_3$)CH$_2$—, —CH(CH$_3$)CH(CH$_3$)—, —CH$_2$C(CH$_3$)$_2$—, —CH$_2$CH(C$_2$H$_5$)—, —CH$_2$CH$_2$CH$_2$—, —CH(CH$_3$)CH$_2$CH$_2$—, —CH$_2$CH(CH$_3$)CH$_2$—, —CH$_2$CH(C$_2$H$_5$)CH$_2$—, —CH$_2$CH$_2$CH(C$_2$H$_5$)—, —C(CH$_3$)$_2$CH$_2$CH$_2$—, —CH(CH$_3$)CH$_2$CH(CH$_3$)—, —CH$_2$CH$_2$CH$_2$CH$_2$—, —CH$_2$C(CH$_3$)$_2$CH$_2$CH$_2$—, —CH$_2$C(CH$_3$)$_2$CH$_2$—, —CH$_2$CH$_2$CH(C$_2$H$_5$)CH$_2$—, —CH$_2$CH$_2$CH$_2$CH$_2$CH$_2$—, —CH(CH$_3$)CH$_2$CH$_2$CH$_2$CH$_2$—, —CH$_2$CH$_2$CH$_2$CH$_2$CH$_2$CH$_2$—, —(CH$_2$)$_{10}$—, and the like. Included within this definition are the terms "$C_1$–$C_4$ alkylidene" and "$C_2$–$C_4$ alkylidene".

The term "$C_4$–$C_8$ cycloalkyl" refers to a cycloalkyl ring of four to eight carbon atoms, such as cyclobutyl, cyclopentyl, cyclohexyl, 4,4-dimethylcyclohexyl, cycloheptyl, cyclooctyl, and the like.

The term "straight or branched chain divalent hydrocarbyl residue of one to eight carbon atoms" refers to a divalent radical derived from a straight or branched alkane, alkene, or alkyne of one to eight carbon atoms. Depending upon the branching and number of carbon atoms, as will be appreciated by organic chemists, such a moiety can contain one, two or three double or triple bonds, or combinations of both. As such, this term can be considered an alkylidene group as defined above containing from 1 to 8 carbon atoms optionally containing one to three double or triple bonds, or combinations of the two, limited as noted in the preceding sentence.

This invention includes the pharmaceutically acceptable base addition salts of the compounds of Formula I. Such salts include those derived from inorganic bases, such as ammonium and alkali and alkaline earth metal hydroxides, carbonates, bicarbonates, and the like, as well as salts derived from basic organic amines, such as aliphatic and aromatic amines, aliphatic diamines, hydroxy alkylamines, and the like. Such bases useful in preparing the salts of this invention thus include ammonium hydroxide, potassium carbonate, sodium bicarbonate, calcium hydroxide, methyl amine, diethyl amine, ethylene diamine, cyclohexylamine, ethanolamine, and the like. The potassium and sodium salt forms are particularly preferred.

This invention includes both mono-salt forms, i.e., a 1:1 ratio of a compound of Formula I with a base as previously described, as well as di-salt forms in those instances where a compound of Formula I has two acidic groups. In addition, this invention includes any solvate forms of the compounds of Formula I or salts thereof, such as ethanol solvates, hydrates, and the like.

It is recognized that in compounds having branched alkyl, alkylidenyl, or hydrocarbyl functionality, and in those compounds bearing double or triple bonds, various stereoisomeric products may exist. This invention is not limited to any particular stereoisomer but includes all possible individual isomers and mixtures thereof. The term "5-tetrazolyl" refers to both tautomers, ie, (1H)-5-tetrazolyl and (2H)-5-tetrazolyl.

PREFERRED EMBODIMENTS

A most preferred group of compounds employed in the methods of the present invention are those compounds of Formula Ia:

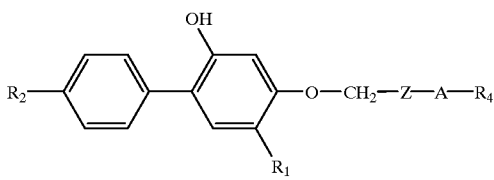

and pharmaceutically acceptable base addition salts thereof. Especially preferred are those compounds wherein $R_2$ is halo, particularly fluoro. Preferred $R_1$ substituents are propyl and especially ethyl.

Preferred Z substituents include $C_2$-$C_4$ alkylidene, particularly —$CH_2CH_2$— and —$CH_2CH_2CH_2CH_2$—. Preferred A groups include —O—, —$CH_2$—, —CH($R_7$-substituted phenyl)-, and —C($CH_3$)$_2$—.

Preferred $R_4$ groups include —COOH, 5-tetrazolyl, or a mono-, di-, or tri-cyclic group as drawn above wherein there is at least one acidic group attached to a ring, such as -W-COOH, -T-G-COOH, or the corresponding tetrazole derivatives. The preferred W moiety is that of a bond or straight chain $C_1$-$C_4$ alkylidene; preferred G moieties are straight chain $C_1$-$C_4$ alkylidene. It is preferred that $R_5$ or $R_7$ be $C_1$-$C_4$ alkyl, especially n-propyl.

Particularly preferred groups are those wherein A is —CH($R_7$-substituted phenyl)- and $R_4$ is —COOH or 5-tetrazolyl. Also preferred are those compounds wherein A is —O— and $R_4$ is

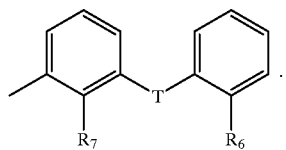

Preferred aspects of this substructure are those wherein $R_7$ is $C_1$-$C_4$ alkyl, especially n-propyl, and $R_6$ is -W-COOH. Particularly preferred are those compounds wherein T is —O— or —S— and W is a bond.

Particularly preferred compounds of the instant invention include 2-[2-propyl-3-[3-[2-ethyl-4-(4-fluorophenyl)-5-hydroxyphenoxy]propoxy]phenoxy]benzoic acid; 3-(2-(3-(2-ethyl-4-(4-fluorophenyl)-5-hydroxyphenoxy)propoxy)-6-(4-carboxyphenoxy)phenyl)propionic acid; 1-(4-(carboxymethoxy)phenyl)-1-(1H-tetrazol-5-yl)-6-(2-ethyl-4-(4-fluorophenyl)-5-hydroxyphenoxy)hexane; 3-[4-[7-carboxy-9-oxo-3-[3-[2-ethyl-4-(4-fluorophenyl)-5-hydroxyphenoxy]propoxy]-9H-xanthene]]propanoic acid; 5-[3-[2-(1-carboxy)ethyl]-4-[3-[2-ethyl-4-(4-fluorophenyl)-5-hydroxyphenoxy]propoxy]phenyl]-4-pentynoic acid or a pharmaceutically acceptable salt or solvate thereof.

The leukotriene $B_4$ (LTB$_4$) antagonists employed in the methods of the present invention may be synthesized essentially as described in U.S. Pat. No. 5,462,954 issued Oct. 31, 1995, the entire contents of which are herein incorporated by reference.

The following examples further illustrate the preparation of the intermediates and compounds employed in this invention. The examples are illustrative only and are not intended to limit the scope of the invention. Melting points were determined on a Thomas-Hoover apparatus and are uncorrected. NMR spectra were determined on a GE QE-300 spectrometer. All chemical shifts are reported in parts per million (_) relative to tetramethylsilane. Chemical shifts of aromatic protons of quinoline species in DMSO-$d_6$ are concentration dependent. The following abbreviations are used to denote signal patterns: s=singlet, d=doublet, t=triplet, q=quartet, b=broad, m=multiplet. Infrared spectra were determined on a Nicolet DX10 FT-IR spectrometer. Mass spectral data were determined on a CEC-21-110 spectrometer using electron impact (EI) conditions, a MAT-731 spectrometer using free desorption (FD) conditions, or a VG ZAB-3F spectrometer using fast atom bombardment (FAB) conditions. Silica gel chromatography was performed using ethyl acetate/hexane gradients unless otherwise indicated. Reverse-phase chromatography was performed on MCI CHP20P gel using an acetonitrile/water or methanol/water gradient unless otherwise indicated. Tetrahydrofuran (THF) was distilled from sodium/benzophenone ketyl immediately prior to use. All reactions were conducted under argon atmosphere with stirring unless otherwise noted. Where structures were confirmed by infra-red, proton nuclear magnetic resonance, or mass spectral analysis, the compound is so designated by "IR", "NMR", or "MS", respectively.

EXAMPLE 1

3-[2-[3-[(5-Ethyl-2-hydroxy[1,1'-biphenyl]-4-yl)oxy]propoxy]-1-dibenzofuran]propanoic acid disodium salt

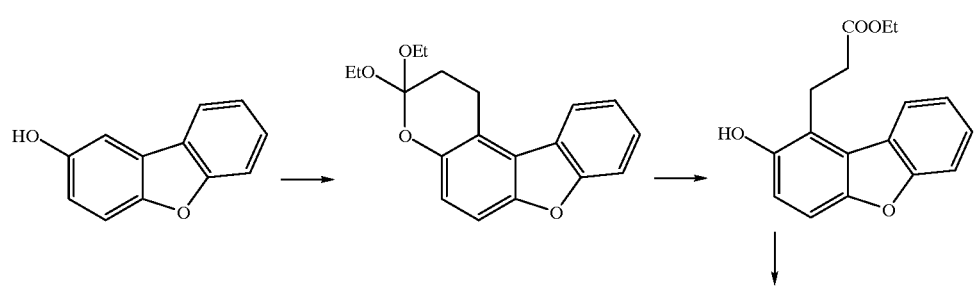

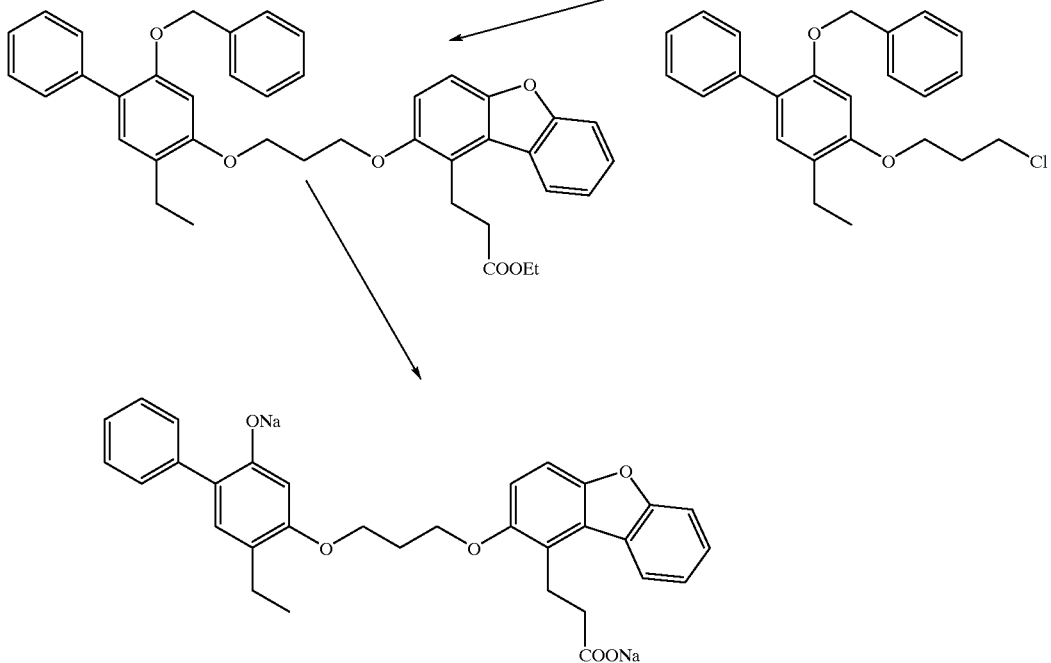

A. Preparation of 3,3-diethoxy-2,3-dihydro-1H-benzofuro-[3,2-f][1]benzopyran.

A solution of 2-hydroxydibenzofuran (5.00 g, 27.2 mmol), triethylorthoacrylate (10.1 g, 54.3 mmol) and pivalic acid (1.39 g, 13.6 mmol) in toluene (100 mL) was refluxed for 18 hours. The mixture was cooled to room temperature and washed once with water and once with a saturated sodium bicarbonate solution, dried over sodium sulfate, filtered and concentrated in vacuo to provide an orange oil. This material was diluted with hexane and maintained at −20° C. for 18 hours. The resulting crystals were collected via vacuum filtration to provide 5.67 g (67%) of the desired title intermediate, mp 64° C.; NMR (CDCl$_3$) 7.96 (d, J=7.8 Hz, 1H), 7.57 (d, J=8.0 Hz, 1H), 7.46 (t, J=8 Hz, 1H), 7.35 (m, 2H), 7.06 (d, J=8.8 Hz, 1H), 3.82 (q, J=7.2 Hz, 2H), 3.73 (q, J=6.8 Hz, 2H), 3.35 (t, J=6.9 Hz, 2H), 2.29 (t, J=7.0 Hz, 2H), 1.23 (t, J=7.1 Hz, 6H); MS-FD m/e 312 (p); IR (CHCl$_3$, cm$^{-1}$) 2982, 1494, 1476, 1451, 1434, 1251, 1090, 1054, 975.

Analysis for $C_{19}H_{20}O_4$: Calc: C, 73.06; H, 6.45; Found: C, 72.81; H, 6.72.

B. Preparation of 3-[1-(2-hydroxydibenzofuran)]propanoic acid ethyl ester.

A mixture of 3,3-diethoxy-2,3-dihydro-1H-benzofuro[3,2-f][1]benzopyran (3.50 g, 11.2 mmol) and 10% aqueous hydrochloric acid (5 mL) in ethyl acetate (30 mL) was stirred at room temperature for 1 hour. The resulting mixture was washed once with water, dried over sodium sulfate, filtered and concentrated in vacuo to provide a tan solid. Recrystallization from hexane/ethyl acetate provided 3.11 g (98%) of the desired title intermediate as an off-white crystalline material: mp 128–131° C.; NMR (CDCl$_3$) 7.88 (d, J=7.7 Hz, 1H), 7.59 (d, J=8.4 Hz, 1H), 7.47 (t, J=7.2 Hz, 1H), 7.37 (d, J=8.9 Hz, 1H), 7.36 (t, J=6.6 Hz, 1H), 7.13 (d, J=8.8 Hz, 1H), 7.13 (q, J=8.8 Hz, 2H), 3.43 (t, J=5.8 Hz, 2H), 3.01 (t, J=7.7 Hz, 2H), 1.23 (t, J=7.2 Hz, 3H); MS-FD m/e 284 (100, p), 256 (65), 238 (17); IR (KBr, cm$^{-1}$) 2985 (b), 1701, 1430, 1226, 1183, 1080.

Analysis for $C_{17}H_{16}O_4$: Calc: C, 71.82; H, 5.67; Found: C, 71.90; H, 5.43.

C. Preparation of 3-[2-[3-[[5-ethyl-2-(phenylmethoxy)-[1,1'-biphenyl]-4-yl]oxy]propoxy]-1-dibenzofuran]propanoic acid ethyl ester.

3-[1-(2-Hydroxydibenzofuran)]propanoic acid ethyl ester (625 mg, 2.20 mmol) was dissolved in dimethylformamide (10 mL) and carefully treated at room temperature with 95% sodium hydride (58 mg, 2.4 mmol). When gas evolution had ceased, 2-benzyloxy-1-phenyl-5-ethyl-4-(3-chloro-1-propyloxy)benzene (836 mg, 2.20 mmol) was added and the resulting mixture was stirred for 18 hours. The mixture was diluted with ether and washed once with water. The organic layer was dried over sodium sulfate, filtered, and concentrated in vacuo to provide a dark oil. Silica gel chromatography (ethyl acetate/hexane) provided 200 mg (14%) of the desired titled intermediate as a colorless oil: NMR (CDCl$_3$) 8.11 (d, J=7.7 Hz, 1H), 7.57 (m, 3H), 7.48 (t, J=7.3 Hz, 1H), 7.20–7.44 (m, 10 H), 7.17 (s, 1H), 7.08 (d, J=8.9 Hz, 1H), 6.67 (s, 1H), 5.05 (s, 2H), 4.29 (t, J=6.2 Hz, 2H), 4.26 (t, J=6.1 Hz, 2H), 4.15 (q, J=7.2 Hz, 2H), 3.54 (t, J=8.5 Hz, 2H), 2.67 (m, 4H), 2.37 (t, J=6.0 Hz, 2H), 1.21 (m, 6H).

D. Preparation of 3-[2-[3-[(5-ethyl-2-hydroxy[1,1'-biphenyl]-4-yl)oxy]propoxy]-1-dibenzofuran]propanoic acid disodium salt.

To a nitrogen-purged solution of 3-[2-[3-[[5-ethyl-2-(phenylmethoxy)[1,1'-biphenyl]-4-yl]oxy]propoxy]-1-dibenzofuran]propanoic acid ethyl ester (200 mg, 0.318 mmol) in a 1:1 mixture of methanol/tetrahydrofuran (40 mL) was added 10% palladium on carbon (25 mg). The resulting suspension was hydrogenated at 1 atm pressure for 24 hours at room temperature. The mixture was filtered through a short pad of Florisil® and the filtrate concentrated in vacuo. The residue was dissolved in a 1:1 mixture of methanol/tetrahydrofuran (20 mL) and treated with 5N sodium hydroxide solution (2 mL) at room temperature for 24 hours.

The resulting mixture was extracted once with diethyl ether. The aqueous layer was acidified with 5N hydrochloric acid solution and extracted twice with methylene chloride. The combined methylene chloride fractions were concentrated in vacuo. The residue was dissolved in a minimum of 1N sodium hydroxide solution and purified on HP-20 resin to provide 53 mg (30%) of the desired title product as a fluffy white solid: NMR (DMSO-$d_6$) 8.12 (d, J=6.9 Hz, 1H), 7.64 (d, J=8.2 Hz, 1H), 7.37–7.57 (m, 5H), 7.30 (m, 2H), 7.14 (m, 2H), 6.96 (s, 1H), 6.93 (s, 1H), 4.30 (t, J=7.3 Hz, 2H), 4.14 (t, J=5.4 Hz, 2H), 2.48 (m, 4H), 2.23 (m, 4H), 1.10 (t, J=7.6 Hz, 3H); MS-FAB m/e 555 (88, p+1), 533 (62); IR (CHCl$_3$, cm$^{-1}$) 3384 (b), 2969, 1566, 1428, 1257, 1181.

Analysis for $C_{32}H_{28}O_6Na_2$: Calc: C, 69.31; H, 5.09; Found: C, 69.51; H, 5.39.

EXAMPLE 2

7-Carboxy-9-oxo-3-[3-(2-ethyl-5-hydroxy-4-phenylphenoxy)propoxy]-9H-xanthene-4-propanoic acid disodium salt monohydrate

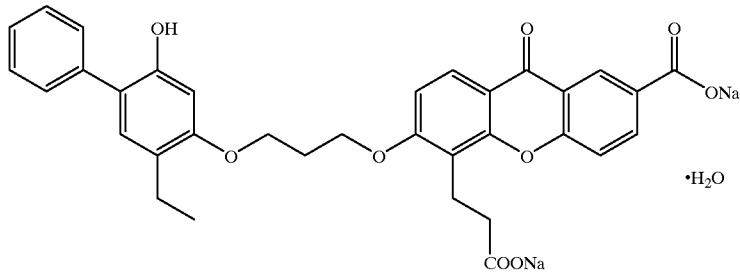

A mixture of 2-benzyloxy-1-phenyl-5-ethyl-4-(3-chloro-1-propyloxy)benzene (749 mg, 1.97 mmol), ethyl 7-carboethoxy-3-hydroxy-9-oxo-9H-xanthene-4-propanoate (729 mg, 1.97 mmol), potassium carbonate (1.36 g, 9.85 mmol) and potassium iodide (33 mg, 0.20 mmol) was refluxed for 24 hours. Dimethylsulfoxide (2 mL) was added and heating continued for 24 hours. The reaction mixture was cooled to room temperature, diluted with ethyl acetate, and washed once with water. The organic layer was dried over sodium sulfate, filtered and concentrated in vacuo to reveal a tan solid. This material was dissolved in ethyl acetate (30 mL) and the resulting solution purged with nitrogen. To this solution was added 10% palladium on carbon (120 mg) and the resulting suspension hydrogenated at 1 atmosphere of pressure. The solution was filtered and concentrated in vacuo to provide a colorless oil. This material was dissolved in a solution of 1:1 methanol/tetrahydrofuran (30 mL) and treated with 5N sodium hydroxide solution (2 mL) at room temperature for 18 hours. The resulting solution was extracted once with diethyl ether and the aqueous layer acidified with 5N hydrochloric acid solution. The resulting precipitate was collected via suction filtration. This material was converted to the di-sodium salt and purified as described above for the preparation of Example 1(D) to provide 390 mg (56%) of the desired title product as a fluffy white solid: NMR (DMSO-$d_6$) 12.65 (s, 1H, —OH), 8.65 (s, 1H), 8.28 (dd, J=8.5, 2.0 Hz, 1H), 8.01 (d, J=8.9 Hz, 1H), 7.50 (m, 3H), 7.29 (t, J=7.8 Hz, 2H), 7.17 (m, 2H), 6.93 (s, 1H), 6.89 (s, 1H), 4.26 (m, 4H), 3.12 (m, 2H), 2.47 (m, 2H), 2.23 (m, 2H), 1.10 (t, J=7.4 Hz, 3H); MS-FAB m/e 627 (24, p), 605 (40), 583 (24), 331 (24), 309 (100); IR (KBr, cm$^{-1}$) 3419 (b), 2962, 1612, 1558, 1443, 1390, 1277, 1084.

Analysis for $C_{34}H_{28}O_9Na_2 \cdot H_2O$: Calc: C, 63.34; H, 4.69; Found: C, 63.36; H, 4.50.

EXAMPLE 3

2-[2-Propyl-3-[3-[2-ethyl-4-(4-fluorophenyl)-5-hydroxyphenoxy]propoxy]phenoxy]benzoic acid sodium salt

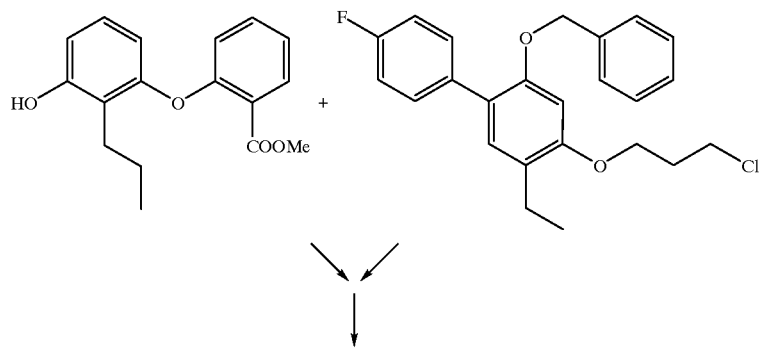

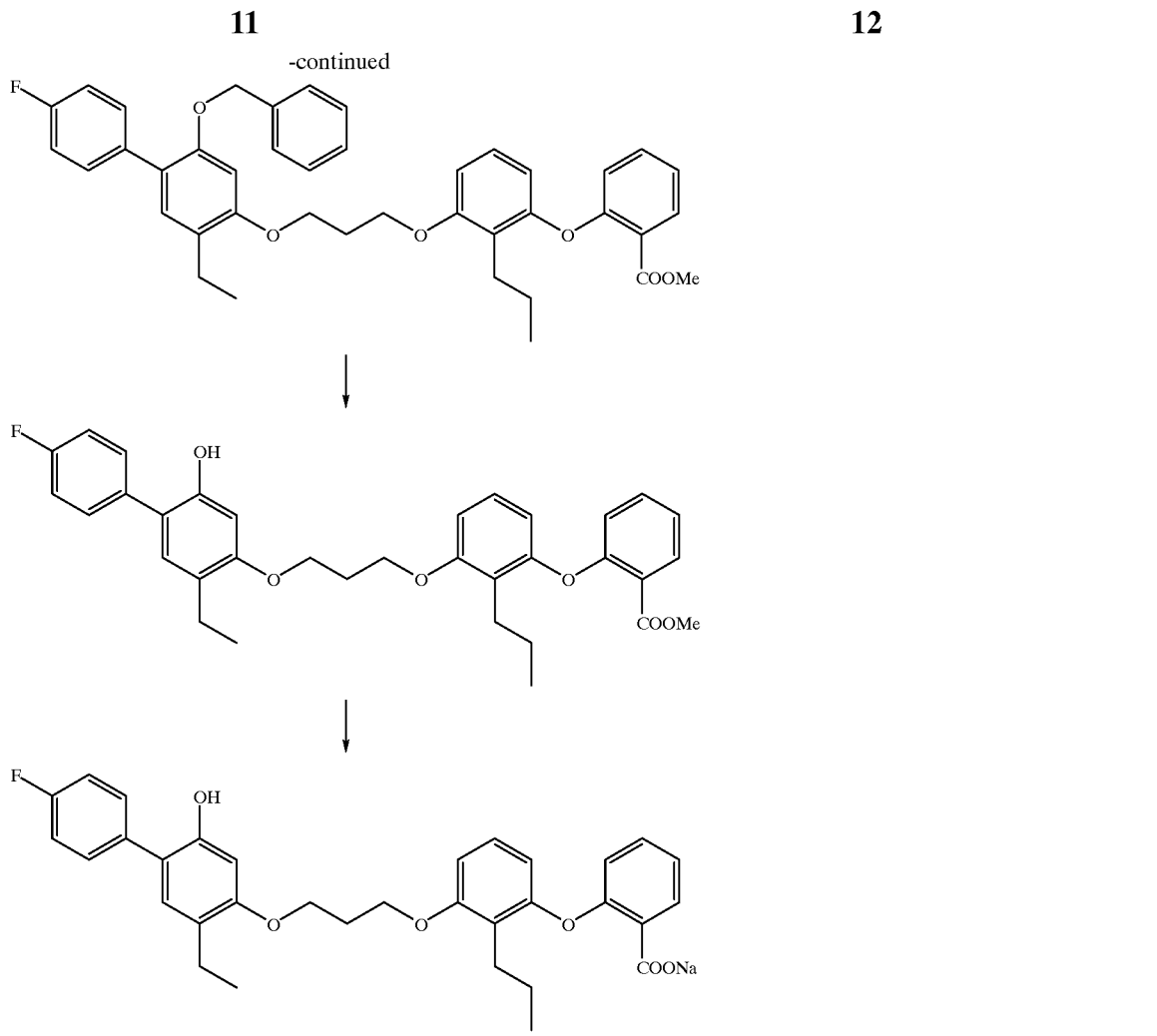

A. Preparation of 2-[2-propyl-3-[3-[2-ethyl-4-(4-fluorophenyl)-5-(phenylmethoxy)phenoxy]propoxy]phenoxy]benzoic acid methyl ester.

A mixture of 2-benzyloxy-1-(4-fluorophenyl)-5-ethyl-4-(3-chloro-1-propyloxy)benzene (20.0 g, 50.2 mmol) and sodium iodide (75.3 g, 502 mmol) in 2-butanone (200 mL) was refluxed for 6 hours. The mixture was diluted with ether and washed once with water. The organic layer was dried over sodium sulfate, filtered, and concentrated in vacuo to provide a colorless oil. This material was dissolved in dimethylformamide (100 mL) and treated with 2-(3-hydroxy-2-propylphenoxy)benzoic acid methyl ester (14.4 g, 50.2 mmol) and potassium carbonate (20.8 g, 151 mmol) at room temperature for 24 hours. This mixture was diluted with water and twice extracted with ether. The aqueous layer was separated and back-extracted once with ethyl acetate. The combined organic layers were dried over sodium sulfate, filtered, and concentrated in vacuo to provide a yellow oil. Silica gel chromatography provided 25.4 g (78%) of the desired title intermediate as a pale golden oil: NMR (CDCl$_3$) 7.91 (d, J=7.8 Hz, 1H), 7.54 (d, J=8.6 Hz, 1H), 7.52 (d, J=8.5 Hz, 1H), 7.25–7.43 (m, 6H), 7.03–7.38 (m, 5H), 6.84 (d, J=8.3 Hz, 1H), 6.71 (d, J=8.1 Hz, 1H), 6.63 (s, 1H), 6.47 (d, J=8.1 Hz, 1H), 5.03 (s, 2H), 4.24 (t, J=5.7 Hz, 2H), 4.21 (t, J=5.8 Hz, 2H), 3.86 (s, 3H), 2.69 (t, J=7.8 Hz, 2H), 2.64 (t, J=7.7 Hz, 2H), 2.34 (quintet, J=6.0 Hz, 2H), 1.60 (hextet, J=5.0 Hz, 2H), 1.22 (t, J=7.5 Hz, 3H), 0.94 (t, J=7.5 Hz, 3H); MS-FD m/e 648 (p); IR (CHCl$_3$, cm$^{-1}$) 2960, 1740, 1604, 1497, 1461, 1112.

Analysis for C$_{41}$H$_{41}$O$_6$F: Calc: C, 75.91; H, 6.37; Found: C, 76.15; H, 6.45.

B. Preparation of 2-[2-propyl-3-[3-[2-ethyl-4-(4-fluorophenyl)-5-hydroxyphenoxy]propoxy]phenoxy]benzoic acid methyl ester.

2-[2-Propyl-3-[3-[2-ethyl-4-(4-fluorophenyl)-5-(phenylmethoxy)phenoxy]propoxy]phenoxy]benzoic acid methyl ester (33.0 g, 50.9 mmol) was de-benzylated as described above for the preparation of Example 2 to provide 27.3 g (96%) of the title intermediate as an amber oil: NMR (CDCl$_3$) 7.90 (dd, J=7.8, 1.7 Hz, 1H), 7.42 (m, 3H), 7.05–7.23 (m, 4H), 6.99 (s, 1H), 6.84 (d, J=8.1 Hz, 1H), 6.70 (d, J=8.1 Hz, 1H), 6.55 (s, 1H), 6.46 (d, J=8.1 Hz, 1H), 5.05 (s, 1H, —OH), 4.23 (m, 4H), 3.86 (s, 3H), 2.68 (t, J=7.4 Hz, 2H), 2.62 (q, J=7.5 Hz, 2H), 2.36 (quintet, J=6.0 Hz, 2H), 1.60 (hextet, J=7.7 Hz, 2H), 1.20 (t, J=7.6 Hz, 3H), 0.94 (t, J=7.4 Hz, 3H); MS-FD m/e 558 (p); IR (CHCl$_3$, cm$^{-1}$) 2965, 1727, 1603, 1496, 1458, 1306, 1112.

Analysis for C$_{34}$H$_{35}$O$_6$F: Calc: C, 73.10; H, 6.31; Found: C, 73.17; H, 6.42.

C. Preparation of 2-[2-propyl-3-[3-[2-ethyl-4-(4-fluorophenyl)-5-hydroxyphenoxy]propoxy]phenoxy]benzoic acid sodium salt.

2-[2-Propyl-3-[3-[2-ethyl-4-(4-fluorophenyl)-5-hydroxyphenoxy]propoxy]phenoxy]benzoic acid methyl ester (21.5 g, 38.5 mmol) was hydrolyzed as described above for the preparation of Example 2. The acid was converted to the sodium salt and purified as described above for the preparation of Example 1(D) to provide 16.7 g (77%) of the desired title product as a white amorphous solid: NMR (DMSO-$d_6$) 10.50 (bs, 1H, —OH), 7.51 (m, 3H), 7.20 (t, J=7.4 Hz, 1H), 7.13 (m, 2H), 7.00 (m, 2H), 6.95 (s, 1H), 6.67 (dd, J=8.2, 3.3 Hz, 2H), 6.62 (s, 1H), 6.26 (d, J=8.2 Hz, 1H), 4.14 (t, J=5.8 Hz, 2H), 4.02 (t, J=5.7 Hz, 2H), 2.60 (t, J=6.8 Hz, 2H), 2.47 (q, J=7.3 Hz, 2H), 2.16 (t, J=5.9 Hz, 2H), 1.45 (hextet, J=7.5 Hz, 2H), 1.07 (t, J=7.5 Hz, 3H), 0.81 (t, J=7.4 Hz, 3H); MS-FAB m/e 568 (38, p+1), 567 (100, p), 544 (86), 527 (77), 295 (65), 253 (45); IR (KBr, cm$^{-1}$) 3407 (b), 2962, 1603, 1502, 1446, 1395, 1239, 1112.

Analysis for $C_{33}H_{32}O_6FNa$: Calc: C, 69.95; H, 5.69; F, 3.35; Found: C, 69.97; H, 5.99; F, 3.52.

The methods of the present invention describe the use of leukotriene antagonists for the treatment or inhibition of iritis which is characterized by the excessive release of leukotriene $B_4$.

The term "excessive release" of a leukotriene refers to an amount of the leukotriene sufficient to cause iritis. The amount of leukotriene which is considered to be excessive will depend on a variety of factors, including the amount of leukotriene required to cause the disease, and the species of the mammal involved. As will be appreciated by those skilled in the art, the success of treating a mammal suffering from or susceptible to iritis characterized by an excessive release of leukotriene with a compound of Formula I will be measured by the regression or prevention of the symptoms of the condition.

ASSAYS

Assay 1

The effectiveness of compounds of Formula I to inhibit the binding of tritiated $LTB_4$ to guinea pig lung membranes was determined as follows.

[$^3$H]-$LTB_4$ Radioligand Binding Assay in Guinea Pig Lung Membranes

[$^3$H]-$LTB_4$ (196–200 Ci/mmole) was purchased from New England Nuclear (Boston, Mass.). All other materials were purchased from Sigma (St. Louis, Mo.). Incubations (555 mL) were performed in polypropylene minitubes for 45 minutes at 30° C. and contained 25 mg of guinea pig lung membrane protein (Silbaugh, et al., *European Journal of Pharmacology*, 223 (1992) 57–64) in a buffer containing 25 mM MOPS, 10 mM $MgCl_2$, 10 mM $CaCl_2$, pH 6.5, approximately 140 pM [$^3$H]-$LTB_4$, and displacing ligand or vehicle (0.1% DMSO in 1 mM sodium carbonate, final concentration) as appropriate. The binding reaction was terminated by the addition of 1 mL ice cold wash buffer (25 mM Tris-HCl, pH 7.5) followed immediately by vacuum filtration over Whatman GF/C glass fiber filters using a Brandel (Gaithersburg, Md.) 48 place harvester. The filters were washed three times with 1 mL of wash buffer. Retained radioactivity was determined by liquid scintillation counting at 50% counting efficiency using Ready Protein Plus cocktail (Beckman, Fullerton, Calif.). Nondisplaceable binding was determined in the presence of 1 mM $LTB_4$ and was usually less than 10% of total binding. Data were analyzed using linear regression analysis of log-logit plots of the values between 10% and 90% of control binding to calculate $IC_{50}$s and slope factors (pseudo-Hill coefficients). $IC_{50}$ values thus obtained were corrected for radioligand concentration (Cheng and Prusoff, *Biochem. Pharmacol.*, 22, 3099 (1973)) to calculate $K_i$ values. pKi is the mean $-\log K_i$ for n experiments.

Compounds of the instant invention tested in the above assay were found to have a pKi of between 7 and 11.

The ability of compounds of formula I to treat eye inflammation can be evaluated in two models, allergen-induced conjunctivitis in guinea pigs (Garceau et al., *European J. Pharmacol.*, 143, 1–7, 1987) and endotoxin-induced uveitis in rats (Okumura et al., *Int. Ophtalmol.* 14, 31–6, 1990).

Assay 2

Allergen-Induced Conjunctivitis Model

Male guinea pigs, weighing approximately 300 grams are sensitized by injecting intraperitoneally 0.5 ml of a suspension containing 10 μg of ovalbumin and 0.1 gram of aluminum hydroxide in saline. Two weeks later, animals are challenged topically twice, 24 hours apart, on the eye with 10 μl of a 2.5% (w/v) solution of ovalbumin dissolved in saline. In the absence of an inhibitor, increased microvascular permeability (measured by assaying for the extravasation of a radioactively-labeled protein from the vasculature into the conjunctival tissue) and neutrophil infiltration (assayed by measuring myeloperoxidase activity in the conjunctiva) can be observed 30 minutes after the second antigen challenge. Some of the response occurring is due to release of histamine and $LTD_4$. This can be masked by pretreating the animals 30 minutes before antigen challenge intravenously with mepyramine (2.0 mg/kg) and zafirlukast (1 μmole/kg). A compound of formula I in 10 μl of vehicle is applied topically 20 minutes before the second challenge.

Assay 3

Endotoxin-Induced Vreitis Model

In the uveitis model, Salmonella endotoxin (1 mg/rat) is injected into the foot pads of Lewis rats. Eighteen hours later, maximum increases of cells and proteins occur in the anterior chamber in the absence of any anti-inflammatory agent. Three doses of a compound of formula I in 10 μl vehicle are applied topically at 5 hour intervals following injection of the endotoxin. Dose-response effects are obtained by dividing the animals into 4 experimental groups of 10 rats each. The groups are treated with either vehicle, 0.5, 1.0, or 2.0% (w/v) of a compound of formula I in 0.5% hydroxyethyl-cellulose. The effectiveness of a treatment is accessed by comparing the enhanced fluid and cell infiltration in either the conjunctiva or aqueous humor of the treated group to that of the vehicle control.

Acute iritis can be characterized by moderately severe pain and photophobia with moderately decreased vision. Transparent precipitates may be present on the posterior surface of the cornea. Intraocular pressure is usually normal or soft and lacrimation is often present along with circumcorneal hyperemia. The iris may appear dull and swollen, the pupil small and irregular with minimal pupillary response to light.

The therapeutic and prophylactic treatments provided by this invention are practiced by administering to a mammal in need thereof a dose of a compound of formula I or a pharmaceutically acceptable salt or solvate thereof, that is effective to inhibit or treat iritis.

The term "inhibit" includes its generally accepted meaning which includes prohibiting, preventing, restraining and slowing, stopping or reversing progression, severity or a resultant symptom. As such, the present method includes both medical therapeutic and/or prophylactic administration as appropriate.

While it is possible to administer a compound employed in the methods of this invention directly without any formulation, the compounds are usually administered in the form of pharmaceutical formulation comprising a pharmaceutically acceptable excipient and at least one compound of the present invention. The compounds or formulations of the present invention may be administered by the oral and rectal routes, topically, parenterally, e.g., by injection and by continuous or discontinuous intra-arterial infusion, in the form of, for example, tablets, lozenges, sublingual tablets, sachets, cachets, elixirs, gels, suspensions, aerosols, ointments, for example, containing from 0.01 to 90% by weight of the active compound in a suitable base, soft and hard gelatin capsules, suppositories, injectable solutions and suspensions in physiologically acceptable media, and sterile packaged powders adsorbed onto a support material for making injectable solutions. Such formulations are prepared in a manner well known in the pharmaceutical art and comprise at least one active compound. See, e.g., REMINGTON'S PHARMACEUTICAL SCIENCES, (16th ed. 1980).

In making the formulations employed in the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable carriers, excipients and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, tragacanth, gelatin, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compounds of this invention may be delivered transdermally using known transdermal delivery systems and excipients. Most preferably, a compound of this invention is admixed with permeation enhancers including, but not limited to, propylene glycol, polyethylene glycol monolaurate, and azacycloalkan-2-ones, and incorporated into a patch or similar delivery system. Additional excipients including gelling agents, emulsifiers, and buffers may be added to the transdermal formulation as desired.

For topical administration, a compound of this invention ideally can be admixed with any variety of excipients in order to form a viscous liquid or cream-like preparation.

For oral administration, a compound of this invention ideally can be admixed with carriers and diluents and molded into tablets or enclosed in gelatin capsules.

In the case of tablets, a lubricant may be incorporated to prevent sticking and binding of the powdered ingredients in the dies and on the punch of the tableting machine. For such purpose there may be employed for instance aluminum, magnesium or calcium stearates, talc or mineral oil.

Preferred pharmaceutical forms of the present invention include capsules, tablets, creams and ointments. Especially preferred are creams and ointments.

The therapeutic and prophylactic treatments provided by this invention are practiced by administering to a mammal in need thereof a dose of a compound of formula I or a pharmaceutically acceptable salt or solvate thereof that is effective to inhibit or treat iritis.

Advantageously for this purpose, formulations may be provided in unit dosage form, preferably each dosage unit containing from about 5 to about 500 mg (from about 5 to 50 mg in the case of parenteral or inhalation administration, and from about 25 to 500 mg in the case of oral or rectal administration) of a compound of Formula I. Dosages from about 0.5 to about 300 mg/kg per day, preferably 0.5 to 20 mg/kg, of active ingredient may be administered although it will, of course, readily be understood that the amount of the compound or compounds of Formula I actually to be administered will be determined by a physician, in the light of all the relevant circumstances including the condition to be treated, the choice of compound to be administered and the choice of route of administration and therefore the above preferred dosage range is not intended to limit the scope of the present invention in any way.

The specific dose of a compound administered according to this invention to obtain therapeutic or prophylactic effects will, of course, be determined by the particular circumstances surrounding the case, including, for example, the route of administration the age, weight and response of the individual patient, the condition being treated and the severity of the patient's symptoms.

In general, the compounds of the invention are most desirably administered at a concentration that will generally afford effective results without causing any serious side effects and can be administered either as a single unit dose, or if desired, the dosage may be divided into convenient subunits administered at suitable times throughout the day.

While all of the compounds illustrated above exemplify $LTB_4$ inhibition activity in vitro, we have also discovered that compounds bearing a single acidic group ($R_6$) are considerably more orally bioactive when administered to mammals compared with those compounds bearing two such acidic groups. Thus, a preferred embodiment when administering compounds of Formula I orally to mammals comprises administering compounds bearing a single acidic $R_6$ functionality.

The following formulation examples may employ as active compounds any of the compounds of this invention. The examples are illustrative only and are not intended to limit the scope of the invention in any way.

Formulation 1

Hard gelatin capsules are prepared using the following ingredients:

|  | Quantity (mg/capsule) |
| --- | --- |
| 3-(2-(3-(2-Ethyl-4-(4-fluorophenyl)-5-hyroxyphenoxy)propoxy)-6-(4-carboxyphenoxy)phenyl)propanoic acid | 250 |
| Starch | 200 |
| Magnesium stearate | 10 |

The above ingredients are mixed and filled into hard gelatin capsules in 460 mg quantities.

Formulation 2

A tablet is prepared using the ingredients below:

| | Quantity (mg/tablet) |
|---|---|
| 1-(4-(Carboxymethoxy)phenyl)-1-(1H-tetrazol-5-yl)-6-(2-ethyl-4-(4-fluorophenyl)-5-hydroxyphenoxy)hexane | 250 |
| Cellulose, microcrystalline | 400 |
| Silicon dioxide, fumed | 10 |
| Magnesium stearate | 5 |

The components are blended and compressed to form tablets each weighing 665 mg.

Formulation 3

An aerosol solution is prepared containing the following components:

| | Weight % |
|---|---|
| 3-[4-[7-Carboxy-9-oxo-3-[3-[2-ethyl-4-(4-fluorophenyl)-5-hydroxyphenoxy]propoxy]-9H-xanthene]]propanoic acid | 0.25 |
| Ethanol | 30.00 |
| Propellant 11 (trichlorofluoromethane) | 10.25 |
| Propellant 12 (Dichlorodifluoromethane) | 29.75 |
| Propellant 114 (Dichlorotetrafluoroethane) | 29.75 |

The active compound is dissolved in the ethanol and the solution is added to the propellant 11, cooled to −30° C. and transferred to a filling device. The required amount is then fed to a container and further filled with the pre-mixed propellants 12 and 114 by means of the cold-filled method or pressure-filled method. The valve units are then fitted to the container.

Formulation 4

Tablets each containing 60 mg of active ingredient are made up as follows:

| | |
|---|---|
| 2-[2-Propyl-3-[3-[2-ethyl-5-hydroxy-4-(4-fluorophenyl)phenoxy]propoxy]phenoxy]-benzoic acid sodium salt | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50–60° and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules each containing 80 mg of medicament are made as follows:

| | |
|---|---|
| 5-[3-[2-(1-Carboxy)ethyl]-4-[3-[2-ethyl-4-(4-fluorophenyl)-5-hydroxyphenoxy]propoxy]-phenyl]-4-pentynoic acid | 80 mg |
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

Formulation 6

Suppositories each containing 225 mg of active ingredient are made as follows:

| | |
|---|---|
| 3-(2-(3-(2-Ethyl-4-(4-fluorophenyl)-5-hydroxyphenoxy)propoxy)-6-(4-carboxy-phenoxy)phenyl)propanoic acid | 250 |
| Starch | 200 |
| Magnesium stearate | 10 |

The active ingredient is passed through a No. 60 mesh U.S. sieve and suspended in the fatty acid glycerides previously melted using the minimum heat necessary. The mixture is then poured into a suppository mold of nominal 2 g capacity and allowed to cool.

Formulation 7

Suspensions each containing 50 mg of medicament per 5 mL dose are made as follows:

| | |
|---|---|
| 2-[2-Propyl-3-[3-[2-ethyl-4-(4-fluorophenyl)-5-hydroxyphenoxy]propoxy]phenoxy]benzoic acid | 50 mg |
| Sodium carboxymethyl cellulose | 50 mg |
| Sugar | 1 g |
| Methyl paraben | 0.05 mg |
| Propyl paraben | 0.03 mg |
| Flavor | q.v. |
| Color | q.v. |
| Purified water to | 5 mL |

The medicament is passed through a No. 45 mesh U.S. sieve and mixed with the sodium carboxymethylcellulose, sugar, and a portion of the water to form a suspension. The parabens, flavor and color are dissolved and diluted with some of the water and added, with stirring. Sufficient water is then added to produce the required volume.

Formulation 8

An intravenous formulation may be prepared as follows:

| | |
|---|---|
| 2-[2-propyl-3-[3-[2-ethyl-4-(4-fluorophenyl)-5-hydroxyphenoxy]propoxy]phenoxy]benzoic acid | 100 mg |

| Isotonic saline | 1,000 ml |
| --- | --- |

The solution of the above ingredients generally is administered intravenously to a subject at a rate of 1 ml per minute.

We claim:

1. A method for treating or inhibiting iritis in a mammal which comprises administering to a mammal in need thereof an effective amount of a compound of the formula I

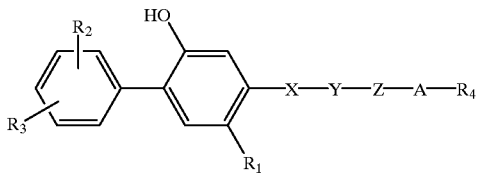

wherein:

$R_1$ is $C_1$–$C_5$ alkyl, $C_2$–$C_5$ alkenyl, $C_2$–$C_5$ alkynyl, $C_1$–$C_4$ alkoxy, ($C_1$–$C_4$ alkyl)thio, halo, or $R_2$-substituted phenyl;

each $R_2$ and $R_3$ are each independently hydrogen, halo, hydroxy, $C_1$–$C_4$ alkyl, $C_1$–$C_4$ alkoxy, ($C_1$–$C_4$ alkyl)-S(O)$_q$—, trifluoromethyl, or di-($C_1$–$C_3$ alkyl)amino;

X is —O—, —S—, —C(=O)—, or —CH$_2$—;

Y is —O— or —CH$_2$—;

or when taken together, -X-Y- is —CH=CH— or

Z is a straight or branched chain $C_1$–$C_{10}$ alkylidenyl;

A is a bond, —O—, —S—, —CH=CH—, or —CR$_a$R$_b$-, where R$_a$ and R$_b$ are each independently hydrogen, $C_1$–$C_5$ alkyl, or $R_7$-substituted phenyl, or when taken together with the carbon atom to which they are attached form a $C_4$–$C_8$ cycloalkyl ring;

$R_4$ is $R_6$

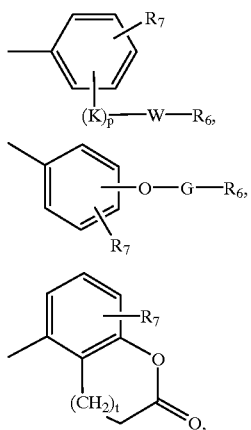

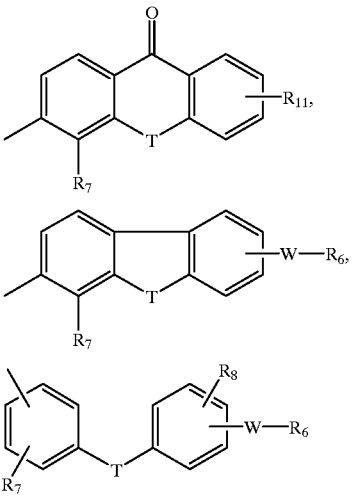

where, each $R_6$ is independently —COOH, 5-tetrazolyl, —CON(R$_9$)$_2$, or —CONHSO$_2$R$_{10}$;

each $R_7$ is hydrogen, $C_1$–$C_4$ alkyl, $C_2$–$C_5$ alkenyl, $C_2$–$C_5$ alkynyl, benzyl, methoxy, -W-R$_6$, -T-G-R$_6$, ($C_1$–$C_4$ alkyl)-T-($C_1$–$C_4$ alkylidenyl)-O—, or hydroxy;

$R_8$ is hydrogen or halo;

each $R_9$ is independently hydrogen, phenyl, or $C_1$–$C_4$ alkyl, or when taken together with the nitrogen atom form a morpholino, piperidino, piperazino, or pyrrolidino group;

$R_{10}$ is $C_1$–$C_4$ alkyl or phenyl;

$R_{11}$ is $R_2$, -W-R$_6$, or -T-G-R$_6$;

each W is a bond or straight or branched chain divalent hydrocarbyl radical of one to eight carbon atoms;

each G is a straight or branched chain divalent hydrocarbyl radical of one to eight carbon atoms;

each T is a bond, —CH$_2$—, —O—, —NH—, —NHCO—, —C(=O)—, or —S(O)$_q$—;

K is —C(=O)— or —CH(OH)—;

each q is independently 0, 1, or 2;

p is 0 or 1; and t is 0 or 1;

provided when X is —O— or —S—, Y is not —O—;

provided when A is —O— or —S—, $R_4$ is not $R_6$;

provided when A is —O— or —S— and Z is a bond, Y is not —O—; and provided W is not a bond when p is 0;

or a pharmaceutically acceptable salt or solvate thereof.

2. The method as claimed in claim 1 employing a compound of the formula

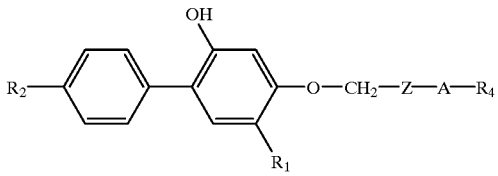

or a pharmaceutically acceptable salt or solvate thereof.

3. The method as claimed in claim 2 employing 2-[2-propyl-3-[3-[2-ethyl-4-(4-fluorophenyl)-5-hydroxyphenoxy]propoxy]phenoxy]benzoic acid or a pharmaceutically acceptable salt or solvate thereof.

4. The method as claimed in claim 2 employing 3-(2-(3-(2-ethyl-4-(4-fluorophenyl)-5-hydroxyphenoxy)propoxy)-6-(4-carboxy-phenoxy)phenyl)propionic acid or a pharmaceutically acceptable salt or solvate thereof.

5. The method as claimed in claim 2 employing 1-(4-(carboxy-methoxy)phenyl)-1-(1H-tetrazol-5-yl)-6-(2-ethyl-4-(4-fluorophenyl)-5-hydroxyphenoxy)hexane or a pharmaceutically acceptable salt or solvate thereof.

6. The method as claimed in claim 2 employing 3-[4-[7-carboxy-9-oxo-3-[3-[2-ethyl-4-(4-fluorophenyl)-5-hydroxyphenoxy]-propoxy]-9H-xanthene]]propanoic acid or a pharmaceutically acceptable salt or solvate thereof.

7. The method as claimed in claim 2 employing 5-[3-[2-(1-carboxy)-ethyl]-4-[3-[2-ethyl-4-(4-fluorophenyl)-5-hydroxyphenoxy]-propoxy]phenyl]-4-pentynoic acid or a pharmaceutically acceptable salt or solvate thereof.

8. The method as claimed in any one of claims 1 to 7 in which the mammal is a human.

\* \* \* \* \*